United States Patent [19]

Vletter

[11] Patent Number: Plant 7,365

[45] Date of Patent: Oct. 23, 1990

[54] LILY PLANT NAMED 'MENTON'

[75] Inventor: Floris Vletter, Rijnsburg, Netherlands

[73] Assignee: Gebr. Vletter & J. H. Den Haan, Netherlands

[21] Appl. No.: 334,486

[22] Filed: Apr. 7, 1989

[51] Int. Cl.[5] ..... A01H 5/00

[52] U.S. Cl. ..... Plt./68

[58] Field of Search ..... Plt./68

[56] References Cited

U.S. PATENT DOCUMENTS

P.P. 6,426 11/1988 McRae ..... Plt. 68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new lily plant named Menton particularly characterized by its soft orange flower color, good forcing, very short exterior and interior petals, and its very narrow, elliptical leaves.

1 Drawing Sheet

1

The present invention comprises a new and distinct cultivar of lily, botanically known as Lilium (Asiatic hybrid), and hereinafter referred to by the cultivar name Menton.

Menton is a product of a planned breeding program which had the objective of creating new lily cultivars with better forcing properties.

Menton was originated by me from a hybridization made in a controlled breeding program in Rijnsburg, The Netherlands beginning in 1982. The female parent was the variety known as Avignon, disclosed in a pending application of applicant. The male parent of Menton was a cultivar identified as G.692.

Menton was discovered and selected by me as one flowering plant within the progeny of the stated cross in June 1984 in a controlled environment in Rijnsburg, The Netherlands.

I accomplished the first act of asexual reproduction of Menton by scaling bulbs of the initial selection in August 1984 in a controlled environment in Rijnsburg. Horticultural examination of selected units initiated in April 1987 has demonstrated that the combination of characteristics as herein disclosed for Menton are firmly fixed and are retained through successive generations of asexual reproduction.

Menton has not been observed under all possible environmental conditions. The phenotype may vary significantly with variations in environment such as temperature, light intensity, and day length. The following observations, measurements, and comparisons describe plants grown in Aalsmeer, The Netherlands under greenhouse conditions which approximate those generally used in commercial practice.

The following traits have been repeatedly observed and are determined to be basic characteristics of Menton which in combination distinguish this lily as a new and distinct cultivar.

1. Its soft orange color.
2. Good forcing characteristics with a soft forcing-time.
3. Interior and exterior petals very short in length, average in width.
4. Its leaves are very narrow in width, short to average in length and narrow, elliptical in shape

2

The accompanying photographic drawing shows typical flower characteristics of Menton, with colors being as true as possible with illustrations of this type.

In the following description, color references are made to The Royal Horticultural Society Color Chart (R.H.S.)

Origin: Seedling.

Name: Menton.

Parentage:

*Female parent.*—Avignon.

*Male parent.*—G.692.

*Classification.*—Asian hybrid.

Plant:

1. *Plant height (on opening of the anthers of the first flower).*—tall 1.35 m.
2. *Stalk.*—anthocyanin coloring present. Color: brown with green flecks. Growth of Hair: present, very weak. Type of coat of hair: long. Division of coat of hair: primarily in leaf axils and upper stalk. Internode length: long, uniform 1.5 cm to 2 cm. Cross section: round. Bulbils: lacking.
3. *Leaf.*—Position: spread out. Top angle of the base with the stalk: sharp, about 45°. Length: short to medium 10.5 cm. Width: vary narrow 1.2 cm. Thickness: normal. Form (middle third part of the stalk): narrow elliptical. Color of the top: medium green R.H.S. 139B. Luster of the top: medium to strong. Growth of hair at the bottom: lacking. Top: pointed. Curve of the edge: lacking. Membranous edge: lacking. Indentation of the edge: lacking. Uniformity: present. Form in cross section: angled. Top part: bent back. Flexibility: strong. Stalk: lacking.

Flower:

1. *Structure.*—Type: umbel. Secondary flowers: none. Growth of hair: present, very weak. Bracts: present. Number of bracts in comparison with the number of primary flowers: equal. Bracteole: present. Number of bracteoles in comparison with the total number of flowers: equal. Position: erect to horizontal. Type: bowl-shaped. Cross-section: medium. Height of crown: short. Length of longest flower stalk: average 12 cm.

Typical flower count: Five (5) to six (6) blooms at one time and continuous, from bulb size 16/18.

2. *Petal.*—Length of longest exterior petal: very short 9 cm. Width of widest exterior petal: average 3.8 cm. Length of longest interior petal: very short 8.5 cm. Width of widest interior petal: average 4.8 cm. Color of the inside of the interior petal: orange 25C at base and along the edges; elsewhere lighter, 24C. Color of the outside of the interior petal: light orange with green vein. Color of the inside of the exterior petal: orange 25C at base and along the edges; elsewhere lighter, 24C. Color of the outside of the exterior petal: soft orange R.H.S. 24C–25C, with greenish lines in median. Marking on the inside: present. Color of the marking: dark purple red. Type of marking on the inside: spots, elliptical; approximately 1×1.5 mm. Density of the spots in the marking: about 30 on each of the top 3 petals, specked on each side of and generally extending to slightly above the nectary tubes Color of the inside of the throat: light orange with green. Color of the outside of the throat; greenish. Surface structure of the inside: ribbed and papillate. Luster at the inside: lacking. Curve of the edges of the petal: present. Type of curve of the edge of the petals: fine. Flexure of petals: present. Bended part of the petals: only distal part. Extent of bending: average. Color of flower buds: soft orange with greenish lines in median; difficult to provide accurate color values. Nectaries — coloration and pubescence: Color is darker orange than the color of the petal; very weak pubescence.

Reproductive organs:

*Length of stamens.*—Very short.

*Color of the filaments.*—Orange, more yellow at the top.

*Color of the anthers.*—Purple.

*Color of pollen.*—Dark brown.

*Length of the pistil.*—Short.

*Color of the style.*—Brownish with hint of green.

*Color of the stigma.*—Purple.

Bulb:

Type (in dormant season): Type 2.

Top: Pointed.

Density of scales: Close.

Color of the exterior scales: White.

Length of the exterior scales: Short to average.

Width of the exterior scales: Narrow to average.

Top of the scales: Pointed.

I claim:

1. A new and distinct cultivar of lily plant named Menton, as illustrated and described.

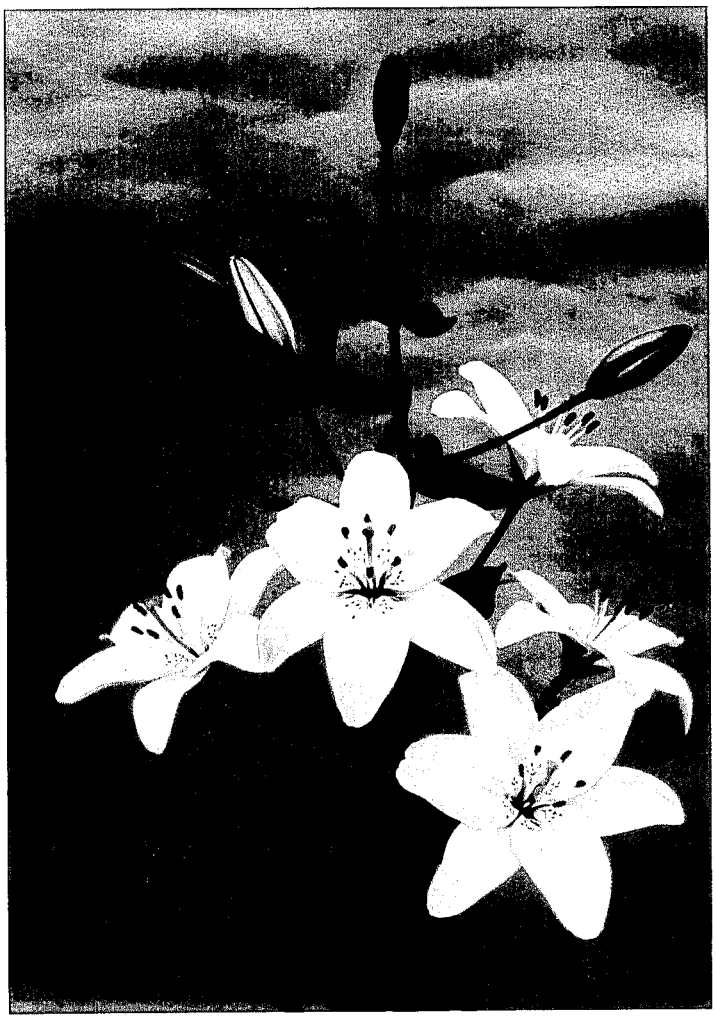

* * * * *